(12) United States Patent
Majewski et al.

(10) Patent No.: US 6,271,525 B1
(45) Date of Patent: Aug. 7, 2001

(54) MINI GAMMA CAMERA, CAMERA SYSTEM AND METHOD OF USE

(75) Inventors: Stanislaw Majewski; Andrew G. Weisenberger, both of Grafton; Randolph F. Wojcik, Yorktown, all of VA (US)

(73) Assignee: Southeastern University Research Assn., Newport News, VA (US)

( * ) Notice: Subject to any disclaimer, the term of this patent is extended or adjusted under 35 U.S.C. 154(b) by 0 days.

(21) Appl. No.: 09/159,177

(22) Filed: Sep. 23, 1998

(51) Int. Cl.[7] ............................. G01T 1/202; G01T 1/208
(52) U.S. Cl. ........................... 250/367; 250/368; 250/369
(58) Field of Search .......................... 250/363.1, 363.02, 250/367, 368, 369, 207, 214 VT

(56) References Cited

U.S. PATENT DOCUMENTS 5,276,615 * 1/1994 Edmond et al. .................. 250/363.1
5,401,969 * 3/1995 Basler ................................ 250/363.1
5,610,967 * 3/1997 Moorman et al. ..................... 378/154
5,864,141 * 1/1999 Majewski et al. .............. 250/363.02

* cited by examiner

Primary Examiner—Georgia Epps
Assistant Examiner—Richard Hanig

(57) ABSTRACT

A gamma camera comprising essentially and in order from the front outer or gamma ray impinging surface: 1) a collimator, 2) a scintillator layer, 3) a light guide, 4) an array of position sensitive, high resolution photomultiplier tubes, and 5) printed circuitry for receipt of the output of the photomultipliers. There is also described, a system wherein the output supplied by the high resolution, position sensitive photomultipiler tubes is communicated to: a) a digitizer and b) a computer where it is processed using advanced image processing techniques and a specific algorithm to calculate the center of gravity of any abnormality observed during imaging, and c) optional image display and telecommunications ports.

6 Claims, 4 Drawing Sheets

MINI GAMMA CAMERA, CAMERA SYSTEM AND METHOD OF USE

The United States of America may have certain rights to this invention under Management and Operating Contract DE-AC05-84ER 40150 from the United States Department of Energy.

FIELD OF THE INVENTION

The present invention relates to an improved high resolution/small field-of-view gamma camera for use in breast cancer and similar anatomical imaging, and to a method for accurately determining the position of lesions and other imaged abnormalities.

BACKGROUND OF THE INVENTION

X-ray mammography is the primary clinical screening tool for breast cancer. Over 15 million mammograms were performed in 1995 and over 25 million are expected to be performed by 2000. However mammography suffers from a high false positive rate. Currently, biopsies are performed following a positive mammogram to determine whether a suspicious lesion is cancerous or benign. Of the approximately 800,00 biopsies performed in 1995, roughly 600,000 were conducted on benign lesions. In addition to the expense involved, biopsy is a stressful procedure for the patient and the scarring left by the biopsy makes subsequent mammograms more difficult to interpret. Additionally, about 15–25% of all women have breast tissue that results in indeterminate mammograms. Dense tissue and scarring from prior surgery have x-ray densities similar to breast lesions, resulting in low contrast mammograms that are difficult to interpret.

Scintimammography has been shown to be able to complement mammography by imaging the metabolic activity of cancerous lesions while ignoring benign lesions and healthy tissue. In studies conducted over the past five years involving 600 women, in connection with the approval process of the DuPont Merck Pharmaceutical Company imaging agent Miraluma™, it was concluded that scintimammography is useful in differentiating cancerous and benign lesions. However, the studies also concluded that current large field-of-view gamma cameras cannot reliably image breast lesions smaller than 1.2–1.5 cm. In addition, the large size of these cameras limits their use to the lateral (side) views and does not allow for imaging the breast from other desirable viewing angles, and lesions in the chest wall are very difficult to detect.

U.S. Pat. No. 5,753,917 to Engdahl issued May 19, 1998 describes a multilayer gamma ray discrimination device comprising a pair of scintillator layers mounted in front of an array of photomultiplier tubes for purposes of discriminating between two types of gamma rays. The photomultipliers are neither position sensitive, nor are they or their capabilities described as high resolution. Each individual photomultiplier is apparently capable of individual detection, however collectively they possess no positioning capability and for this reason would not provide the resolution necessary to produce the resolution and positioning capability required of cameras of the type described and claimed herein.

Through the use of novel gamma detector technology, the camera of the present invention images at a higher resolution than can be achieved with conventional gamma cameras, allowing smaller tumors to be seen. The smaller physical size of the camera of the present invention allows close imaging in both lateral and cranial-caudal (top) views.

SUMMARY OF THE INVENTION

The improved gamma camera of the present invention, through the use of an array of position sensitive, high resolution photomultiplier devices and a camera configuration that effectively eliminates "dead space", in combination with enhanced image analysis techniques, provides a system that is capable of detecting and locating tumors which could not be reliably detected or located with conventional large field-of-view cameras, and allows for the obtaining of close imaging in views that were unobtainable with such large field-of-view cameras.

The gamma camera of the present invention comprises essentially and in order from the front outer or gamma ray impinging surface: 1) a collimator, 2) a scintillator layer, 3) a light guide, 4) an array of position sensitive, high resolution photomultiplier tubes, and 5) printed circuit boards or circuitry for receipt of the output of the photomultiplier. In use, an area of the human body suspected of containing a lesion or other abnormality which has been previously injected with a radiotracer is exposed to the gamma camera of the present invention, the information supplied by the high resolution, position sensitive photomultiplier tubes is communicated to: a) a computer where it is processed using advanced image processing techniques and a specific algorithm to calculate the center of gravity of any abnormality observed during imaging, and b) optional image display and telecommunications ports. The make-up of these various layers and elements, their interactions and additional optional elements desirable for the production of a practical diagnostic tool will be described in greater detail hereinafter.

DESCRIPTION OF THE DRAWINGS

The present invention will be more fully understood from the detailed description given hereinbelow and the accompanying drawings which are given by way of illustration only, are not limitative of the present invention and wherein like numerals indicate like elements.

DETAILED DESCRIPTION OF THE INVENTION

Figure 1:
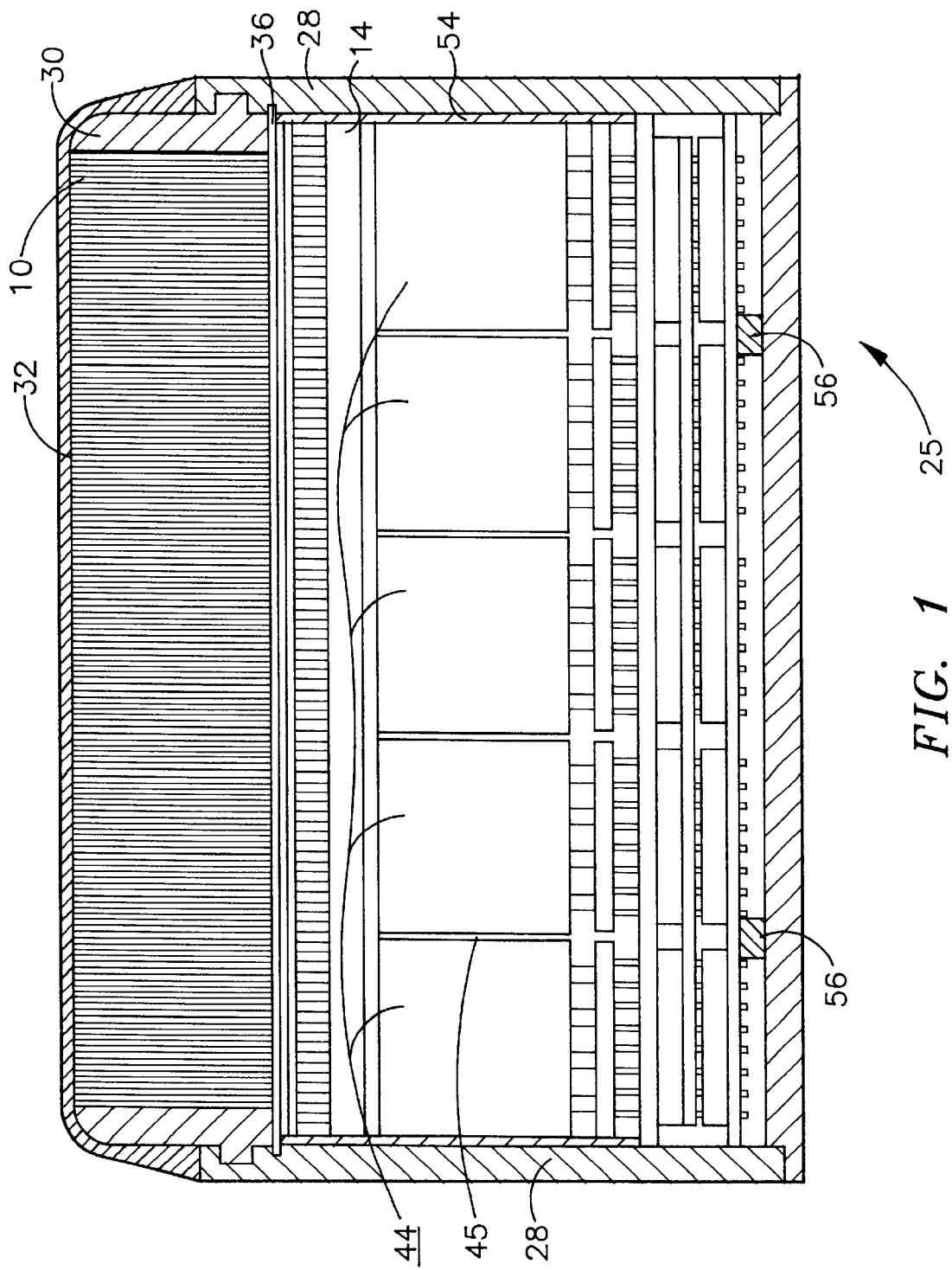
FIG. 1 is a schematic drawing of the system of the present invention.
Figure 2:
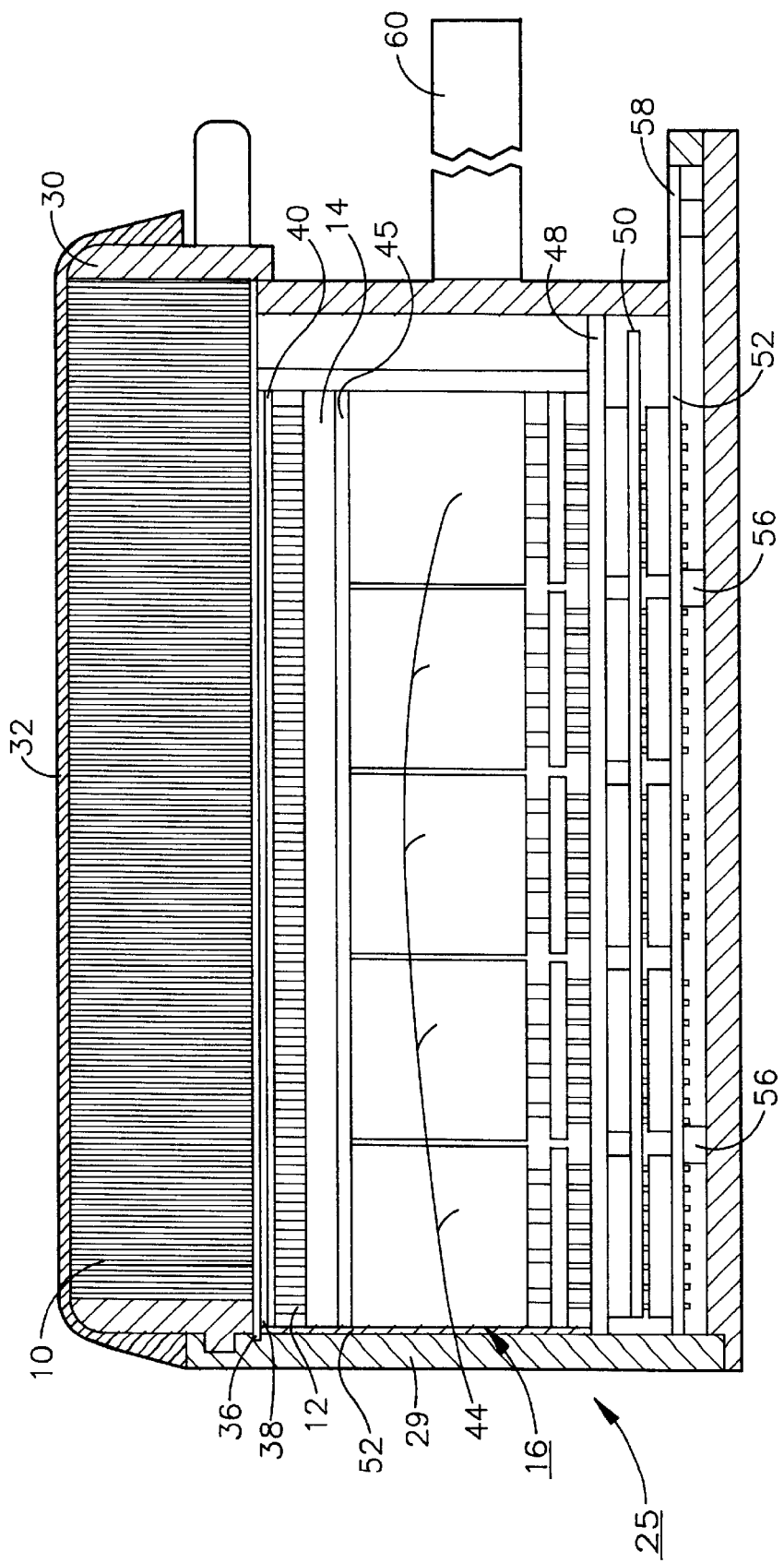
FIG. 2 is a cross sectional view of the gamma camera of the present invention.
Figure 4:
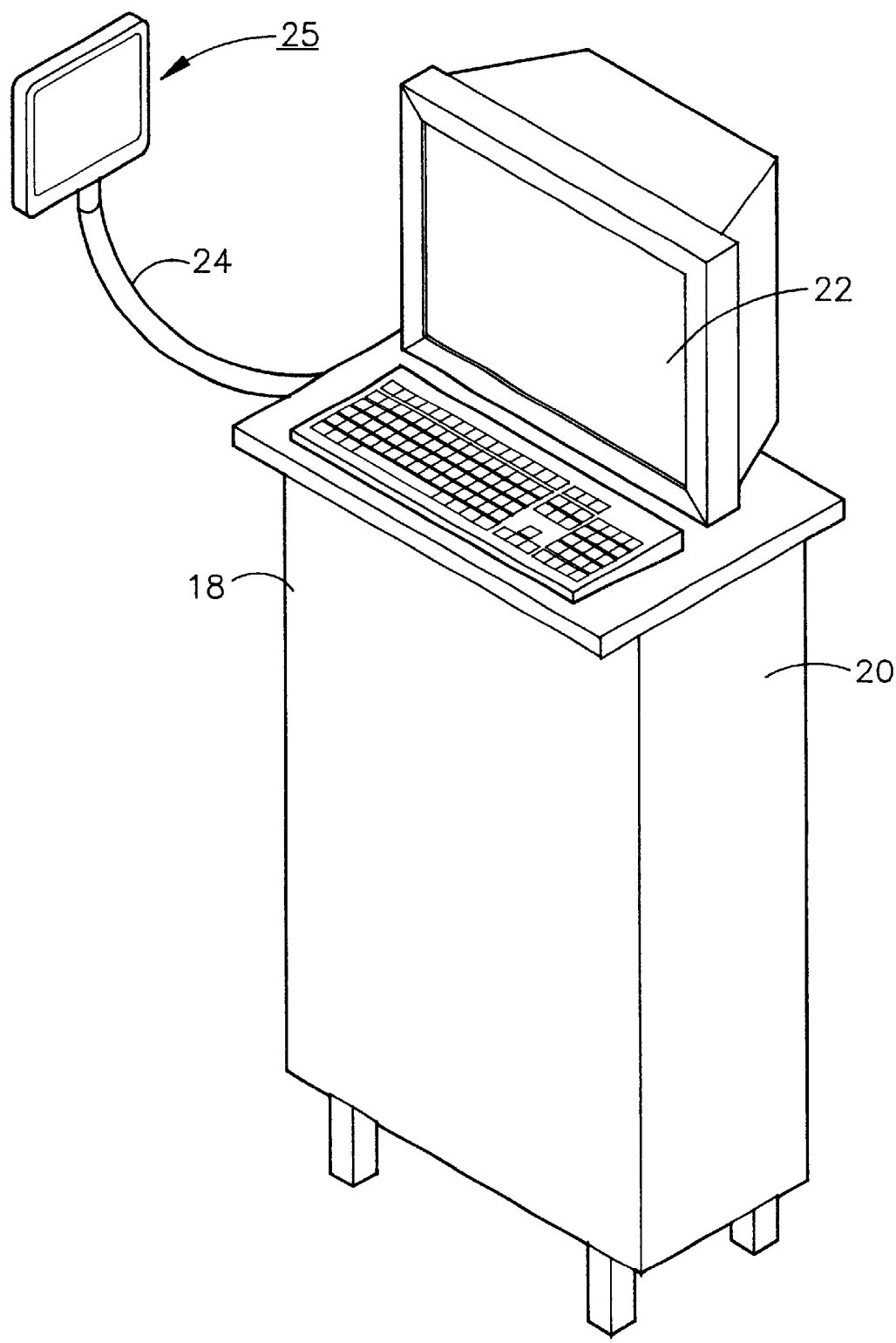
FIG. 4 is a conceptual drawing of the gamma camera of the present invention mounted on an appropriate transport device.

As shown schematically in FIGS. 1 and 2 and in perspective in FIG. 4, the complete scintimammography/gamma camera system of the present invention comprises a collimator 10, a scintillator layer 12, a light guide 14, an array of position sensitive photomultiplier tubes 16, a digitizer 18 which digitizes the output of photomultiplier array 16, a computer 20 wherein image analysis to compute the center of gravity of detected tumor (not shown) is performed and optionally, display 22 which permits an operator to view the image. Communications means, which permit transmission of the image and other information from computer 20 to a remote location, may also be provided.

The heart or core of the system of the present invention is, of course, the novel gamma camera 25 shown schematically in FIG. 2. As shown in this drawing, camera 25 comprises a housing 28 of machineable tungsten, lead or some other suitable material which will trap gamma rays and prevent the dissemination of stray radiation. In this figure, the portion 30 of housing 28 is shown as separate or removable from the main portion of housing 28. This arrangement is merely optional so as to permit easy removal and replacement of collimator 10 described hereinafter. The top or outer surface 32 of camera 25 is preferably of silicone or some other similar non- or minimally heat conductive material for the comfort of the patient to which the camera 25 is applied. As long as the material of layer 32 does not inhibit the passage of gamma rays, its composition is of little import. Preferably, layer 32 is about 1/8" thick when the material of choice is silicone.

The first essential element of the camera is the collimator 10. The purpose of collimator 10, as is well known to those skilled in the art, is to align or "focus" the incoming gamma rays for their subsequent encounter with the scintillator layer. Collimator 10 of camera 25 is of any conventional design and is preferably made of etchable tungsten or lead. According to a preferred embodiment, collimator 10 is of etchable tungsten and is about 1 inch in thickness.

Immediately behind or separated by a small air gap (on the order of 0.010") is a layer 36 of a light impermeable material such as a thin foil of aluminum. A principal purpose of optional layer 36 is to insure that no extraneous light enters the camera and impinges upon the scintillator or the photomultiplier tubes described below. The presence of such stray radiation could, of course, affect any subsequent images produced by the camera. A secondary purpose of layer 36 is to serve to protect the friable scintillator layer 12 from physical damage. According to a preferred embodiment, layer 36 is made of aluminum and is about 0.04" thick.

Behind layer 36 is scintillator layer 12. Scintillator layer 12 may be contiguous with layer 36 or separated therefrom by thin protective compressed foam layer 38. When present, compressed foam layer 38 serves to cushion or protect the friable scintillator layer 12 from physical damage through shock Scintillator layer 12 may be of any conventional scintillator crystal that will produce adequate response to the required incoming dosage of gamma radiation, and such scintillator materials, their design and fabrication is well known in the art. According to a preferred embodiment of the present invention, the scintillator is CeI (Tl) which is coated with a layer 40 of bonding material such as aluminum oxide in an epoxy matrix. When the scintillator of choice is used with a coating of bonding material, scintillator layer 12 is about 3 mm thick and the bonding/protective layer 40 of epoxy bonded Al2O3 is about 1 mm thick The selection of the scintillator and any coating is, of course, a matter of choice well within the capabilities of the skilled artisan, and is not critical to the successful practice of the present invention.

Adjacent behind scintillator layer 12 is light guide 14. Light guide 14 serves to conduct the visible light produced by scintillator layer 12 in response to incoming gamma radiation to underlying photomultiplier array 16. As the visible light is conducted, it is diffused somewhat. This phenomenon is known in the art, and is used to "mask" so-called dead space that occurs at the edges of any photomultiplier. Conventionally, light guides of this type are made of glass, however, we have discovered that a simple and inexpensive acrylic material works equally well Hence, according to a preferred embodiment of the present invention, light guide 14 is made of acrylic and has a thickness of about 3/16".

A critical element of the present invention resides in photomultiplier array 16 that lies behind scintillator layer 12. Photomultiplier array 16 consists of an assembly of generally rectangular individual, position sensitive, high resolution photomultiplier tubes 44. In the case of a preferred embodiment, each of the individual photomultipliers 44 is about one inch square and contains 16 pixels or individual light receptors whose location is tracked as will be described more fully below. According to a highly preferred embodiment, an array of 25 such individual photomultipliers 44 arranged in a square is used and performs as a single position sensitive photomultiplier when electrically connected as described hereinafter. The preferred photomultiplier device for use in gamma camera 25 is Model R5900U-00-C8 produced by Hamamatsu Photonics K.K., 314-5 Shimokanzo, Toyooka Village, Iwata-qun, Shizuoka-ken, 438-0193 Japan. These photomultiplier units are each about 30mm square and demonstrate an effective area about 22mm square. Their spectral response is in the range of 300 to 650 nm with a peak wavelength of 420 nm. Between each of the individual photomultipliers 44 in photomultiplier array 16 is a thin layer 45 of aluminum oxide in an epoxy matrix similar to that coated over photomultiplier array 16. Thin layer 45 serves as the binder which holds photomultiplier array 16 of photomultipliers 44 together and also serves to reflect light which impinges this joint area back toward the appropriate photomultiplier 44 so that no available photons are absorbed or lost in the system.

Behind photomultiplier array 16 is a series of three printed circuit boards 48, 50 and 52, or similar circuitry, which receive the analog output of photomultiplier array 16 and transmit it via cable 24 to a remotely located commercially available digitizer 18. Digitizer 18 is preferably equipped with K-max/K-max NT data acquisition and instrument control software commercially available from Sparrow Corporation, Starkville, Miss.

From digitizer 18 a digital signal is forwarded to a standard computer equipped with image processing software available from Research Systems, Inc., 2995 Wilderness Place, Boulder, Colo. 80301. It is here that image reconstruction and enhancement and image storage is accomplished, and the calculations to determine the position and center of gravity of any imaged lesions are performed.

Figure 3:
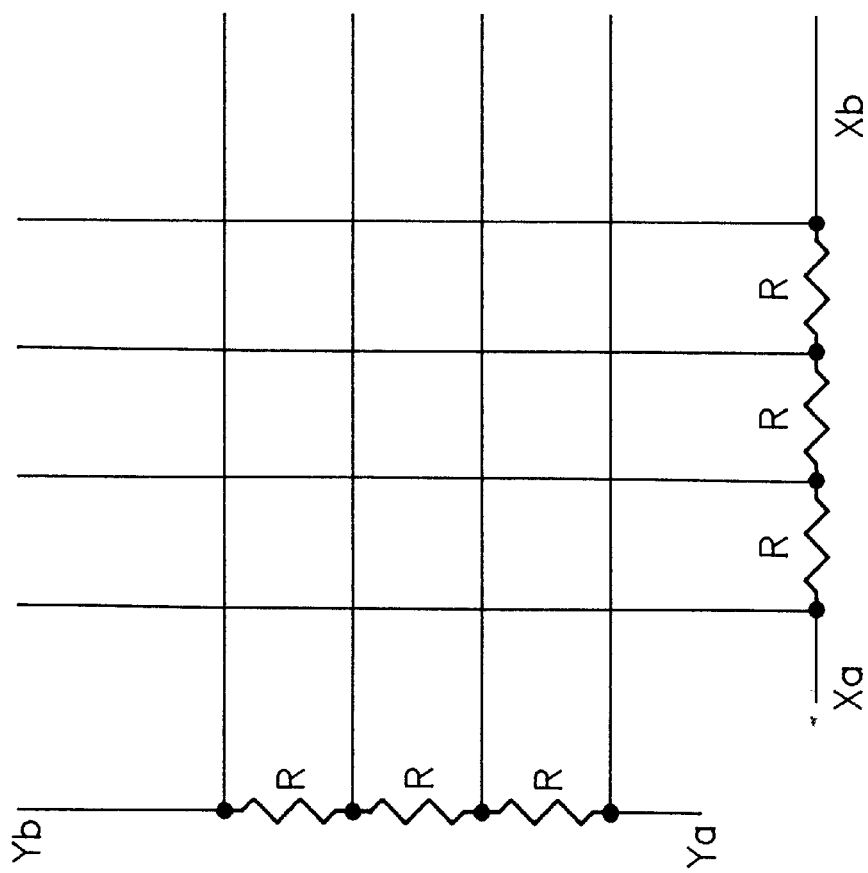
FIG. 3 is a schematic diagram of the charge division readout circuit of the system of the present invention.

The manufacturer of the position sensitive photomultiplier tube, Hamamatsu Inc., has shown that it is possible to obtain submillimeter resolution with these devices if the number of photoelectrons produced by the scintillation light is sufficient. The larger the number of secondary electrons, the better the signal to noise ratio for a given pulse of charge resulting from the photon interaction on the photocathode. This high resolution is possible with an inexpensive charge division readout circuit that can be purchased from Hamamatsu Inc. as an option. FIG. 3 is a schematic diagram of the charge division readout circuit demonstrating how the signals from each anode in the same axis are joined together with single resistors.

To simplify the figure, only four anode wires are shown in the schematic. The amplitude of the charge pulse detected at Xa and Xb, and at Ya and Yb are used to determine the X and Y location of the center of the secondary electron shower. This readout method only requires four signals to be read out by the data acquisition electronics. The disadvantage of the charge division readout is that the information about the distribution of the signal on the individual anode wires is lost since only the integrated signal is preserved.

In applications, such as with the detection of the low energy gamma-ray and x-ray emissions, if the number of photoelectrons is not sufficient to achieve the maximum designed intrinsic resolution of the position sensitive photomultiplier tube, the charge division method will prove inadequate. Moreover, a non-linear spatial response occurs when the peak of the secondary electron cloud distribution is near the edge of the sensitive area and therefore the peak is no longer symmetrical This non-linear spatial response has the effect of limiting the useful active area of individual photomultiplier tube 44. The best way to extract as much information of the extent of secondary electron shower so as to determine the center of gravity of the electron distribution is to read out, individually, each anode wire. The electronic signals appearing at the anode wires are converted to digital signals by way of standard analog to digital converters. It is from these digitized signals that the centroid of the electron cloud needs to be computed.

Determination of the position of gamma interaction in the scintillator is determined by computing a centroid of the signal distribution on the x and y anode sectors of the position sensitive photomultiplier tube. The following equation demonstrates the centroid calculation to determine position (X) of the interaction by using the counts ($C_n$) for each anode wire (Xn).

$$X = \frac{\sum_{n=1}^{total} Xa \cdot Cn}{\sum_{n=1}^{total} Cn}$$

When the centroid of the electron cloud is calculated for the event occurring in the center of the detector, the location of the interaction point is calculated with minimal distortion because of the overall symmetry. However, an edge effect occurs when a photon is detected near the outer perimeter of the area covered by the photocathode as there is an asymmetry in the detection of charge distribution. This asymmetry results in a shift of the computed centroid value towards the center of the detector. Therefore, a resulting "crowding" of the image at the edges of the detector is observed. This is demonstrated when an image of a mask made from a regular array of holes in a lead plate is produced.

A way to partially compensate for this image distortion is to exclude or truncate from the center of gravity calculation the anode wire sectors that carry low signals. The calculation of the truncated centroid is accomplished by using only the digitized signal of those anode wires in the calculation that have an empirically determined optimum fraction of the sum of the anode signals This truncation fraction (F) is typically 5% and is determined experimentally by conducting imaging trials using various fraction values.

The use of this truncated centroid technique is essential to maximizing use of the active area of the position sensitive photomultiplier tube. Using too large truncation values constrains the center of gravity calculation to too few channels and results in distortions by producing artifacts in the form of spikes in the image.

The number of channels to amplify, digitize and readout is reduced by two, through connecting adjacent pairs of anode wires in the position sensitive photomultiplier tube. The original number of anode wires built into the position sensitive photomultiplier are necessary to provide the maximum performance in applications that have a sufficient number of photoelectrons and the charge division readout method is used. This technique of pairing anode wires in a multi-anode position sensitive photomultiplier tube is analogous to choosing the optimum width and spacing of the cathode strips of a detector used in high energy physics research known as multi-wire proportional chambers. To minimize electronics in the multi-wire proportional chambers, it has been shown that a centroid calculation to localize the positive ion avalanche only requires three cathode strips to be read out if the charge avalanche is centered about these strips.

The data acquisition system is CAMAC basd uses a Macintosh Power PC workstation or similar device as the host computer and is interfaced to the CAMAC crate using commercially available software. AB data acquisition and computer imaging control software was developed with the Kmax data acquisition development system purchased from Sparrow Corporation. The Kmax data acquisition system allows the user to construct software "instruments" to control the flow of data from the analog-to-digital converters in electronic modules in the CAMAC crate to the host computer. In addition, the Kmax development system makes it possible to perform real-time computations on the data and to display the data as one and two dimensional histograms.

Digitization of the charge on the anode wires of the position sensitive photomultiplier tube is achieved by using CAMAC charge analog-to-digital converters (ADCs). The signals from the paired anode wires of the position sensitive photomultiplier tube are first amplified with LeCroy TRA1000 monolithic preamplifiers. The signal from the last dynode of the position sensitive photomultiplier tube is inverted and then passed through discriminator electronics to generate a timing signal This signal is used to gate the analog-to-digital converters after it passes through a logic circuit. The purpose of the discriminator electronics is to restrict the generation of output gate pulses to dynode pulses that exceed an empirically determined threshold level. The threshold level was set high enough to exclude low energy noise, but was still low enough to allow the passage of essential pulses.

Other optional elements of gamma camera 25 are shown in FIG. 2. These include: an electrical insulation layer 54 (preferably of acetal or some similar material) about the interior of machined tungsten housing 28 to insure against the possibility of electrical shock; polymeric standoffs 56 (preferably of nylon or some similar material) which secure and cushion printed circuit boards 48, 50 and 52 and are located between printed circuit boards 48, 50, and 52 and housing 28; connector 58 which allows electrical connection of printed circuit board 52 to digitizer 18; and mounting bar 60 for attachment of gamma camera 25 to a suitable transport console 62 as shown in FIG. 4.

As shown in FIG. 4, because of its relatively small size, less than about 6 inches square according to a preferred embodiment, the gamma camera 25 is easily mounted to a maneuverable gantry 64 which can in turn be mounted on a suitable console or transport device 62 which may contain digitizer 18, computer 20 and display 22 as well as appropriate power supplies (not shown).

Figure 5:
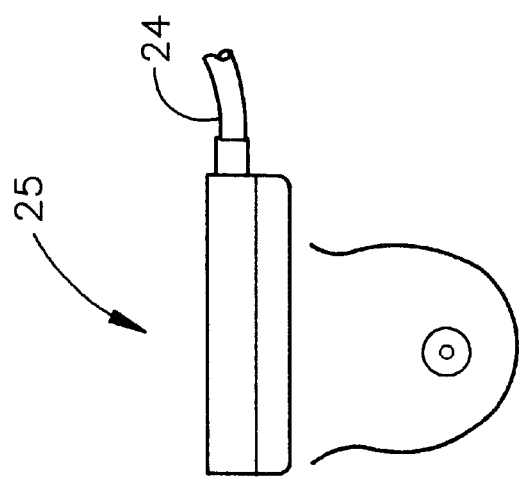
FIG. 5 shows the gamma camera of the present invention in juxtaposition with a female breast as it would be applied in scintimammography.

As Shown in FIG. 5, the relatively small size of gamma camera 25 permits its location adjacent the breast in virtually any desired position with a substantially complete, useful field of view.

As the invention has been described, it will be apparent to those skilled in the art that it may be varied in many ways without departing from the spirit and scope of the invention. Any and all such modifications are intended to be included within the scope of the appended claims.

What is claimed is:

1. A gamma camera comprising:
   1) a collimator;
   2) a scintillator layer comprising a matrix of parallel scintillator crystals held together by a layer of reflecting material;
   3) a light guide;
   4) an array of position sensitive, high resolution photomultiplier tubes having x and y anode sectors providing an output;
   5) printed circuitry for receipt of the output of the photomultiplier tubes;
   6) a digitzer; and
   7) a computer including image processing software where said image processing software determines the center of gravity calculation of the signals disturbed on the X and Y anode sectors of said position sensitive, high resolution photomultiplier tubes by truncating from the center of gravity calculation the anode sectors that carry low signals.

2. The gamma camera of claim 1 wherein each of the position sensitive, high resolution photomultiplier tubes is capable of resolution below about 1 mm.

3. The gamma camera of claim 1 wherein each of the position sensitive, high resolution photomultiplier tubes in comprised of at lest 16 pixels.

4. The gamma camera of claim 1 wherein each of the position sensitive, high resolution photomultiplier tubes is equipped with a charge division readout circuit.

5. The gamma camera of claim 1 further including image display and at least one telecommunication port.

6. A method for determining the existence and defining the position of a lesion of other similar abnormality in the human body comprising the steps of:
   I. exposing an area of the human body suspected of containing the lesion of other abnormality previously injected with a radiotracer to a gamma camera comprising:
      a) a collimator;
      b) a scintillator layer comprising a matrix of parallel scintillator crystals held together by a layer of reflecting material;
      c) a light guide;
      d) an array of position sensitive, high resolution photomultiplier tubes having x and y anode sectors providing an output; and
      e) printed circuitry for receipt of the output of the photomultiplier tubes;
   II. digitizing the output of the photomultiplier tubes; and
   III. providing a computer including imaging processing software where said image processing software determines the center of gravity calculating of the signals distribution on the x and y anode sectors of the position sensitive, high resolution photomultiplier tubes by truncating from the center of gravity calculation the anode sectors that carry low signals.

* * * * *